United States Patent [19]

Herman

[11] Patent Number: 5,190,979
[45] Date of Patent: Mar. 2, 1993

[54] OZONIDES OF TERPENES AND THEIR MEDICAL USES

[76] Inventor: Stephen Herman, 9341 Hazel Cir., Villa Park, Calif. 92667

[21] Appl. No.: 896,735

[22] Filed: Jun. 9, 1992

Related U.S. Application Data

[60] Continuation of Ser. No. 823,087, Jan. 15, 1992, abandoned, which is a continuation of Ser. No. 456,216, Dec. 20, 1989, abandoned, which is a division of Ser. No. 211,378, Jun. 24, 1988, abandoned.

[51] Int. Cl.$^5$ .................. A01N 31/00; A01N 31/04; A61K 31/045; C07C 45/00
[52] U.S. Cl. .................. 514/762; 514/858; 514/859; 514/860; 514/861; 514/862; 514/863; 514/864; 424/DIG. 13
[58] Field of Search ............... 514/762, 858, 859, 860, 514/861, 862, 863, 864; 549/347, 357, 430, 431, 510; 560/205; 568/448, 461, 469, 486, 596, 840, 875, 909.5; 260/410.9 R; 424/DIG. 13

[56] References Cited

U.S. PATENT DOCUMENTS

| 925,590 | 6/1909 | Neel | 549/431 |
|---|---|---|---|
| 1,210,949 | 1/1917 | Knox | 549/431 |
| 1,910,564 | 5/1933 | Rankin | 549/431 |
| 2,083,572 | 6/1937 | McKee | 549/431 |
| 2,243,053 | 5/1941 | Ramage | 549/431 |
| 2,356,062 | 8/1944 | Johnson | 260/410.7 |
| 2,750,411 | 6/1956 | Fisher et al. | 549/431 |
| 3,360,472 | 12/1967 | Renold | 549/431 |
| 3,504,038 | 3/1970 | Beal | 568/469 |
| 4,163,800 | 8/1979 | Wickett et al. | 424/326 |
| 4,451,480 | 5/1984 | DeVillez | 424/278 |
| 4,591,602 | 5/1986 | DeVillez | 514/463 |
| 4,816,478 | 3/1989 | Thornfeldt | 514/450 |

FOREIGN PATENT DOCUMENTS

| 27371 | of 1913 | United Kingdom | 549/431 |
|---|---|---|---|
| 787748 | 12/1957 | United Kingdom | 549/431 |

OTHER PUBLICATIONS

"Immunological Diseases", 4th Edition, Samter, Max Ed., vol. I, pp. 759-760 (1988).
Bailey, et al., *Ozonation of Olefins*, pp. 2-7.
Robert W. Murray, et al. *Cross Diperoxides*, pp. 9-21.
Rudolf Criegee, et al., *Fragmentation of Ozondies*, pp. 22-34.
Tomas Hudlicky, *McGraw-Hill Encyclopedia of Chemistry*, Fifth Edition, 1982, pp. 1035-1038.

*Primary Examiner*—Nathan M. Nutter
*Attorney, Agent, or Firm*—Knobbe, Martens, Olson & Bear

[57] ABSTRACT

Ozonides of terpenes are disclosed. Terpenes which are believed to be pharmacologically active when prepared in accordance with the present invention include: limonene, citronella, alpha-carotene, beta-carotene, Vitamin A, linalool, linalyl acetate, or squalene. Other compounds which are believed to make pharmacologically active terpene ozonides in accordance with the present invention include geraniol, limonene, alpha-pinene, loganin, cymene, farnesanes, eudesmanes, acoranes, cedranes, chamigranes, caryophyllanes, illudanes, humulenes, himachalenes, longifolanes, perhydroazulenes, quaianes, quaianolides, or germacranes. Still other compounds which are believed to make pharmacologically active terpene ozonides in accordance with the present invention include labdanes, clerodanes, abietic acid, phyllocladene, giberellins, ophiobolin A, retigeranic acid, gasgardic acid, lanosterol, euphol, oleanane, ursane, lupeol, hydroxyhopanone, lupanes, or hopanes. Other particular terpene compounds which are believed to make pharmacologically active terpene ozonides when prepared in accordance with the present invention include B-selinene, zingibene, camphene, sabinene, ocimene, myrcene, nerol, citral A, citral B, farnesol, bisabolene, phytol, and cecropia hormone. A method of producing the terpene ozonides is also disclosed. Further, pharmaceutical preparations using these compositions are disclosed. Methods of medical treatment using these pharmaceutical preparations are also disclosed.

16 Claims, No Drawings

OZONIDES OF TERPENES AND THEIR MEDICAL USES

This application is a continuation of application Ser. No. 823,087, filed Jan. 15, 1992, now abandoned, which is a continuation of application Ser. No. 07/456,216, filed Dec. 20, 1989, now abandoned, which is a division of application Ser. No. 211,378, filed Jun. 24, 1988, now abandoned.

BACKGROUND OF THE INVENTION

This invention relates to ozonides of terpene hydrocarbons. More particularly, it relates to formation of terpene trioxyacyclopentanes and pharmaceutical preparations including these compounds for treating or preventing medical conditions. It also relates to methods for preparing certain ozonized terpenes, and to the ozonides prepared by those methods.

Procedures for preparing ozonides of oil-soluble compounds are known in the art, beings disclosed, for example, in U.S. Pat. No. 925,590 to Neel, U.S. Pat. No. 2,083,572 to McKee, and U.S. Pat. No. 4,451,480 to De Villez.

The prior art discloses that some particular types of ozonide structures have certain pharmacological activity. In U.S. Patent No. 925,590, Neel discloses the use of ozonides of terpenes and other ozonides for inhalation therapy, because it was believed to have a therapeutic effect for consumption and asthma. No specific terpene ozonides are disclosed. Although the Neel patent application was filed in 1902, there have apparently been no supporting data reported in the intervening years that corroborate the utility theorized by Neel.

Knox, U.S. Pat. No. 1,210,949 discloses ozonation of castor oil in order to produce a laxative. Ozonation of the oil was believed to reduce its toxicity and create a germicidal effect.

Johnson, U.S. Pat. No. 2,356,062 discloses the use of ozonides of glycerine trioleates for external application, because it was believed that those particular triglycerides had a germicidal, fungicidal and deodorizing effect.

De Villez, U.S. Pat. Nos. 4,451,480 and 4,591,602, discloses use of ozonides of certain fatty acids, including olive oil, sesame oil, jojoba oil, castor oil and peanut oil, for external use as antimicrobial agents, particularly in the treatment of acne. It is believed that at least some of these compounds cause unacceptable skin irritation.

So far as can be determined, none of the medical uses of ozonides described in the prior art have ever been commercialized. Presumably, this lack of commercialization is due to unacceptable side-effects, toxicity, difficulties in storage, or minimal effectiveness. Many of these various compositions decompose on standing. Also, to the extent that the mechanism of action of these compositions can be attributed to their oxygen content, most of the ozonides known in the prior art have been suboptimal because these compounds release no more than 18% of their weight as oxygen.

At any one time, it is estimated that $\frac{1}{3}$ of all women are suffering from bacterial or fungal vaginal infection, and the only presently available treatments are time consuming and the medications used are irritating to mucous membranes. Thus, there is a need for a relatively nonirritating, safe, and effective composition for treatment of these infections.

Genital herpes lesions and Herpes simplex lesions are notoriously resistant to treatment. These viral infections inflict a significant percentage of the population, and there is, at present, no known cure. Nor is there an effective treatment for erupting lesions to lessen or abort the lesions at their initiation. Thus, a need exists for compositions that can treat herpes lesions in at least a palliative manner to minimize the discomfort suffered by those suffering from these diseases.

Chicken pox (Herpes zoster) is a common childhood disease, for which no vaccine is currently known. Lesions of chicken pox cause itching, and may lead to permanent disfigurement, if scratched. Since the disease strikes mainly children, who are unable to resist scratching, the need exists for compositions that can antipruritically treat chicken pox lesions to minimize disfigurement caused by the disease.

External fungal infections, such as athletes foot and onychomycosis (fungal infections of the nails), afflict a large portion of the human population. Similar fungal infections afflict a large percentage of the animal population. Current treatments for external fungal infections are irritating to sensitive individuals, and not always effective. In addition, onychomycosis is difficult to treat, and its incidence appears to be on the rise with the advent of acrylic and other adhesively-mounted artificial nails. Therefore, a need exists for a relatively non-irritating, effective treatment for these infections.

Indolent neoplasms of the skin, such as warts and moles, also afflict a large portion of the human and animal population. Current over-the-counter medications are not always effective, and the only effective therapy in some instances is to have the neoplasms frozen or burned off, necessitating a doctor's visit. Thus, a need exists for a treatment which is effective, and which can be applied by the patient or owner of the afflicted animal.

Steroidal medications are currently in widespread use to relieve the discomforts of bee stings, insect bites, and other dermatoses, such as those caused by psoriasis and those caused by poison oak or poison ivy. While these medications are sometimes effective, their long term use can result in side effects, including thinning of the skin, sleeplessness, physical deformation, improper fat deposition, dependency and others. Thus, there is a need for an effective alternative medication for these ailments.

Symptoms of sunburn can range from mild discomfort to severe burns. This condition occasionally affects virtually the entire population. Current treatments do little more than mask the pain associated with this condition. Products which prevent sunburn, when applied prior to exposure, are currently available. However, there is no product currently available which prevents sunburn symptoms or alleviates the severity of sunburn when applied after exposure to the sun. Many people carelessly or inadvertently expose themselves to the sun without using protective sunscreens. Thus, a need exists for a product that can prevent sunburn after exposure to the sun.

In the treatment of severe burns, prevention of dehydration and infection in the burned patient are major concerns. Currently used therapies for severe burns which address these concerns are often irritating to sensitive burned tissues. Thus, there is a need for a method of treating burns that is non-irritating, yet still effective against both dehydration and infection.

Many adolescents and young adults suffer from acne. Many compounds are currently available to treat acne, with variable effectiveness. The most effective compositions currently known to treat acne use active oxygen to kill the bacteria which are, in part, responsible for the condition. These include benzoyl peroxide. However, these compositions are sometimes irritating, do not always deliver enough oxygen for optimal effectiveness, and can cause drying of the skin. Thus, a need exists for a non-desiccating, effective and non-irritating treatment for acne.

Sexually transmitted diseases (STDs), including herpes, syphilis, gonorrhea and AIDS, are endemic in today's society. Condoms are currently the most effective means of preventing the transmission of these diseases. However, condoms are not 100% effective. A need, therefore, exists for preparations which increase the effectiveness of condoms in preventing the transmission of STDs.

SUMMARY OF THE INVENTION

According to the invention, there are provided novel compounds of ozonized terpene hydrocarbons. A terpene, also known as an isoprenoid, is any of a class of products having a structural relationship to isoprene:

[isoprene structure.]

The ozonized terpenes contain up to 50% oxygen by weight.

The invention also provides methods for producing the terpene ozonides. The terpene ozonides may be produced according to the equation:

under conditions to be more fully described in the Detailed Description of the Invention. The terpene ozonides may also be produced through, inverse ozonolysis procedure described by Y. N. Yurev et al in J. Org. Chem. U.S.S.R. 2, 5 (1975).

The invention, in addition, provides pharmaceutical compositions containing the above novel compounds and a pharmaceutically acceptable carrier. Preferably, these compositions are in dosage form comprising a clinically effective amount of the active compound. In one preferred embodiment of the invention, the pharmaceutical composition is comprised of a compound of the invention in a stable emulsion for injection. In another embodiment, the pharmaceutical composition is comprised of a compound of the invention in a composition suitable for topical application. In still another embodiment, the pharmaceutical composition is in the form of a vaginal cream, foam, or suppository.

The invention, further, provides novel methods of treatment and prevention of a wide variety of medical conditions in humans and other mammals by the application of the above pharmaceutical compositions. Topical application of compounds of the present invention has at least some effectiveness against a wide range of medical conditions. These include, but are not limited to use in treating acne; dermatitis; bacterial infections; fungal infections; viral infections, including those of the herpes type such as herpes simplex, chicken pox (herpes zoster), and genital herpes; the treatment of insect and animal stings and dermatoses caused by poisonous plants and other irritants and allergens; and treatment of indolent neoplasms of the skin, such as warts or moles. It is also useful as an anti-pruritic, in alleviating the symptoms of burns, and in preventing the transmission of STDs, including HIV (Human Immunodeficiency Virus) infection. Systemic injection of compounds of the present invention is further believed to be effective in the treatment of systemic viral, bacterial, and fungal infections, swollen joints, and other conditions.

DETAILED DESCRIPTION OF THE INVENTION

Terpene hydrocarbons are also known as isoprenoids, because they may generally be constructed from isoprene units. Terpene hydrocarbons are usually exact multiples of $C_5H_8$. Terpenes are classified according to the number of isoprene units of which they are composed, as shown in Table 1.

TABLE 1

| 1 hemi- | 5 ses- |
|---------|--------|
| 2 mono- | 6 tri- |
| 3 sesqui- | 8 tetra- |
| 4 di- | n poly- |

While not limiting the scope of the invention, examples of terpenes which may prove especially effective, when used in the method of the preferred embodiment, include limonene, citronella, alpha-carotene, beta-carotene, Vitamin A, linalool, linalyl acetate, and squalene. Other compounds which are believed to make pharmacologically active terpene ozonides in accordance with the present invention include geraniol, limonene, alpha-pinene, loganin, cymene, farnesanes, eudesmanes, acoranes, cedranes, chamigranes, caryophyllanes, illudanes, humulenes, himachalenes, longifolanes, perhydroazulenes, quaianes, quaianolides, and germacranes. Still other compounds which are believed to make pharmacologically active terpene ozonides in accordance with the present invention include labdanes, clerodanes, abietic acid, phyllocladene, giberellins, ophiobolin A, retigeranic acid, gasgardic acid, lanosterol, euphol, oleanane, ursane, lupeol, hydroxyhopanone, lupanes, and hopanes. Other particular terpene compounds which are believed to make pharmacologically active terpene ozonides when prepared in accordance with the present invention include B-selinene, zingibene, camphene, sabinene, ocimene, myrcene, nerol, citral A, citral B, farnesol, bisabolene, phytol, and cecropia hormone. Ozonides of terpenes have three oxygen atoms replacing the double bonds at sites of unsaturation, creating a trioxyacyclopentane.

In the preparation of terpene ozonides, the particular desired terpene starting material is first obtained. A large and representative number of such terpenes are disclosed in the literature and/or are commercially available. (Many terpenes are essential oils that have been isolated from various parts of plants or wood by steam distillation or extraction.)

In the ozonide synthesis, ozone is passed through the terpene under conditions that provide for intimate contact between the terpene starting material and the ozone, such as thin film procedures, sparging, gas entrainment procedures, and the like. On a small scale, for example, the terpene is placed in a vented vessel, and ozone is sparged through the material until the reaction is complete. The ozone may advantageously be generated with any of the commercially-available ozone generators. Such devices include corona discharge tubes through which oxygen gas may be passed. For example, pure oxygen gas passing through an ozone generator will typically leave the device as from 2% to 6% $O_3$ (ozone), with the remainder $O_2$. This ozone mixture may then be sparged through the terpene at ambient temperature and pressure until the reaction is complete.

Completion may be judged by analyzing the gas exiting the ozonation chamber for ozone. (This may be done by passing the exit gas through aqueous potassium iodide and determining whether iodine gas is liberated, or by any other conventional technique.) Alternatively, the reaction may be followed by observing the weight gain of the material undergoing the reaction, by observing changes in physical characteristics (such as conversion from a liquid form to a soft paste), or by simply calculating the quantity of ozone needed to fully ozonate the material and stopping the reaction when a slight excess of ozone has passed through the reaction chamber. Because the reaction is exothermic, its progress may also be followed by monitoring the heat evolved by the reaction medium, and stopping the flow of ozone when the mixture ceases to generate heat.

When the terpene is normally a solid, such as $\beta$-carotene, it may be solubilized in any suitable saturated nonaqueous solvent system prior to ozonation. With all of the terpene ozonides, it is desirable to exclude water, lower alcohols, nucleophilic peroxides, and proton donors from the reaction mixture and from the final composition, in order to prevent premature hydrolysis of the trioxolane ring.

Other suitable ozonation procedures may be used, such as the procedures disclosed in U.S. Pat. Nos. 2,083,572, 3,504,038, and 4,451,480.

In one preferred embodiment of the present invention, the compounds of the present invention are formulated into pharmaceutical preparations. These pharmaceutical preparations include one or more of the terpene ozonides of the present invention, and may further include other pharmaceutically active ingredients. In addition, any of the well-known pharmaceutically-acceptable carriers or excipients may be combined with the compounds of the present invention in a well-known manner. Suitable diluents include, for example, polyethylene glycol, isopropyl myristate, and mineral oil. The pharmaceutical composition may be in any form suitable for topical use, such as an ointment, gel, or cream. Conventional coloring, fragrance and preserving agents may also be provided.

The excellent weight to oxygen ratio of some of the terpene ozonides renders them especially effective in treating many medical conditions. The present invention is capable of releasing large amounts of oxygen, up to 30% of the weight of the compound. This is because terpenes are highly unsaturated compounds. Ozonization of these compounds results in the addition of three oxygen atoms at each site of unsaturation. In addition, the terpene ozonides of the present invention appear to have significant unexpected pharmacological properties that are different in kind or quality from those of unrelated ozonides disclosed in the prior art.

The effective dosage of the compounds of the present invention appears to be much lower than would be expected in light of the prior art, suggesting that the compounds have unexpectedly high efficacy. While the compounds may be used neat (and, indeed, some of them form pharmaceutically elegant creams or ointments, e.g., linalyl ozonide and linalool ozonide), the effective concentration for most topical applications can be as little as 0.01%, by weight. However, the compositions more preferably contain from about 0.5% or 1% to about 10% or 20% by weight active ingredient. Topical compositions containing about 2% or 3% of active ingredient appear to be particularly effective.

For systemic use, such as intravenous, intramuscular, or intraperitoneal injection, the compositions may similarly contain from about 0.01% to about 99% active ingredient, by weight. Preferred systemic compositions contain from about 0.05% to about 20% active ingredient, by weight.

The toxicity of the terpene ozonides appears to be surprisingly low, in both topical and systemic use. Our preliminary data suggest that the $LD_{50}$ for a representative compound, linalool ozonide, is about 3000 mg/kg in mice.

We have discovered that the terpene ozonides of the present invention, when applied topically in suitable pharmacological compositions, are effective for treatment of bacterial, viral, and fungal infections.

In this regard, we have discovered that topical administration of the terpene ozonides of the present invention, in a suitable composition having from about 0.1% to about 50% active ingredient by weight, preferably about 0.5% to about 20% by weight, is effective to minimize the extent and severity of Herpes simplex, genital herpes, and chicken pox lesions, when applied on incipient eruptions.

We have also discovered that vaginal administration of a composition containing the terpene ozonides of the present invention, in a suitable vaginal carrier (such as a suppository, cream, gel, or foam) having from about 0.05% to about 90% active ingredient, by weight, preferably about 0.1% to about 20% by weight, is substantially non-irritating to mucous membrane tissues, and is effective to treat both bacterial and fungal vaginal infections. Administering a spermicidally effective amount of a composition comprising pharmaceutically effective amounts of an ozonide of a terpene in a pharmaceutically acceptable topical or injectable carrier is believed to prevent pregnancy.

Furthermore, we have discovered that topical administration of the terpene ozonides of the present invention, in a suitable composition having from about 0.01% to about 99% or 100% active ingredient, by weight, preferably from about 0.1% to about 25% by weight, is effective in treating fungal infections of the skin and nails, such as athlete's foot and onychomycosis. Similar compositions appear to have a shrinking effect on indolent neoplasms, including warts and moles.

Compositions having from about 0.01% to about 50% active ingredient, preferably about 0.1% to about 20%, are non-irritating to acne affected skin, and have exhibited a strong anti-comedonal effect when used topically on affected areas. It is believed that these compositions deliver nascent oxygen to kill anaerobic bacteria such as *P. acne* when the ozonides undergo hydrolysis. Furthermore, while it is not intended that the applicants be limited to any particular theory or mode of action, it is further believed that the particular ozonolysis fragments (such as ketones or carboxylic acids) formed by terpene ozonides upon release of oxygen have a complimentary pharmacological effect.

Moreover, our data further indicate that topical application of the terpene ozonides of the present invention, after significant exposure to the ultraviolet component of sunlight, is effective in ameliorating the severity of sunburn and facilitating the healing process. Similar reduction of pain, inflammation, and blistering, and an increase in the speed of the healing process has been observed when the composition of the present invention is applied to first and second degree thermal burns on a mammal.

Based on the demonstrated antiviral, antifungal, and antibacterial properties of the present compositions in vitro, and the relatively non-irritating properties of the terpene ozonides, it is further believed that topical administration of the compounds of the present invention can decrease the probability of transmission of sexually transmitted diseases. Thus, for example, the previously described vaginal compositions may be used alone or in conjunction with a condom to decrease the risk of infection. In this regard, the active ingredient may further advantageously be formulated into a lubricating composition of known type.

We have also discovered that topical administration of terpene ozonides in a topical preparation as previously described exhibits significant efficacy in the treatment of most dermatoses, including psoriasis and those dermatoses caused by bee stings, insect bites, poison plants such as poison oak, poison ivy, and stinging nettle, diaper rash, hives, and other reactions for which antihistamine or steroidal medications are commonly prescribed. Administration of the ozonides of the present invention in lieu of steroidal medications is sometimes equally effective; however, side effects are considerably reduced, making terpene ozonide therapy the more desirable treatment. The invention, however, contemplates combination therapy in some instances. Thus, in addition to an effective amount of terpene ozonide, the compositions of the present invention may further include an effective amount of an antihistamine or a corticosteroid. These medications are well known, and effective dosages for the various antihistamines and corticosteroids have been established. When used together with a terpene ozonide, the effective topical concentrations of these ingredients will generally be toward the lower end of the effective range in which they are presently used alone.

The present invention also includes systemic and localized injection of the compositions disclosed herein, including intravascular, intramuscular, subcutaneous, intraperitoneal, and other injection techniques. Such injection may be used for treatment of viral, fungal, and bacterial infection. We have also discovered that localized injection of a terpene ozonide of the present invention into a tumor has an anti-neoplastic effect.

The present invention further includes other suitable pharmacological preparations of terpene ozonides including: medicinal douches, eardrops, eyedrops, throat sprays, dental preparations for topical sores, mouthwashes, armpit deodorants, disinfectant/germicidals, and contact lens sterilization solutions.

EXAMPLE 1 - Preparation of squalene ozonide.

Squalene is ozonized by preparing a solution of 10 g squalene in 100 ml hexane. Ozone gas (4% in oxygen, from a corona discharge ozone generator), is bubbled through this solution via a glass sparger at the rate of 5000 cc/min. The reaction is exothermic, and the reaction temperature is kept within the range of 0° C. to 35° C., preferably 20° C. to 25° C., and more preferably, 22° C. to 24° C., using a cool water bath. The resulting product is the ozonide of beta carotene, and has a 98% weight gain over squalene.

EXAMPLE 2 - Preparation of linalool ozonide.

The ozonide of linalool is prepared by bubbling ozone (4% in oxygen, from a corona discharge ozone generator) through 100 ml neat linalool via a glass sparger. The reaction is exothermic, and the reaction temperature is kept within the range of 0° C. to 35° C., preferably 20° C. to 25° C., and more preferably, 22° C. to 24° C., using a cool water bath. The resulting product is the ozonide of linalool, and has a 31% weight gain over linalool.

EXAMPLE 3 - Preparation of Linalyl Acetate Ozonide

The ozonide of linalyl acetate was prepared by bubbling ozone (4% in oxygen, from a corona discharge ozone generator) through 5 ml neat linanyl acetate at the rate of 5000 cc/min. The reaction mixture was cooled in a water bath, and after 20 minutes, the evolution of heat ceased, indicating completion of the ozonation process. The resulting material had no odor, and was soluble in polyethylene glycol, isopropyl myristate, and mineral oil.

| EXAMPLE 4 - A vaginal suppository for treatment of vaginitis | |
|---|---|
| 2% w/v | Ozonide of linalyl acetate, from Example 3 |
| Balance | Hydrogenated vegetable oil base |
| EXAMPLE 5 - A topical gel effective against burns | |
| 1% w/v | Ozonide of linalool |
| 60% w/v | Carbomer 934 |
| 1% w/v | Disodium edetate |
| 10% w/v | Glycerin |
| Balance | Polyethylene glycol m.w. 400 |
| EXAMPLE 6 - A topical cream effective against acne | |
| 2.5% w/v | Ozonide of linalool |
| 48% w/v | Propylene glycol |
| 30% w/v | Propyl paraben |
| 5% w/v | Polysorbate 60 |
| 10% w/v | Glyceryl monostearate |
| Balance | Mineral oil |
| EXAMPLE 7 - A lubricant for condoms effective against the transmission of STDs | |
| 0.2 g/ml | Ozonide of squalene from Example 1 |
| 10% w/v | Glyceryl stearate |
| 1% w/v | Food-starch modified |
| 2% w/v | Polyethylene glycol m.w. 800 |
| balance | Light mineral oil |
| EXAMPLE 8 - An injectable composition effective against vervucae | |
| 25 mg/ml | ozonide of linalyl acetate from Example 3 |
| balance | Polyethylene glycol m.w. 200 |

EXAMPLE 9 - Test for efficacy of treatment of sunburn

The composition of Example 5 is applied topically to only a portion of the skin surface of a severely sunburned patient in a single application, two hours after the exposure to sunlight. The treated area exhibits slight reddening, but no peeling or blistering. Only minor discomfort is apparent. The untreated area, in contrast, becomes red, blistered, and painful.

EXAMPLE 10 - Test for efficacy of treatment of chicken pox

The composition of Example 5 is topically applied to a portion of the lesions on a child suffering from chicken pox. Within 1 hour, the treated lesions are significantly reduced with little or no self-induced trauma from scratching. The untreated lesions are unchanged in size, and show the effects of trauma from scratching.

EXAMPLE 11 Test for efficacy of treatment of swollen joints

Patients at a sports medicine clinic complaining of swollen knees are divided into three groups: groups A, B and C. The patients in group A receive an injection of the composition of Example 8 into the swollen knee. The patients in group B receive an injection of a placebo, the composition without active ingredient. The patients in group C receive an injection of a corticosteroidal medication. Within 12 hours the swelling in the knees of the patients in group A is significantly reduced. No change is reported in the knees of the patients of group B. The swelling in the knees of the patients of group C is also reduced, however, a significant percentage of the patients suffer inflammatory reactions.

EXAMPLE 12 Test for efficacy of treatment of fungal infections of the vagina

The suppository of Example 4 is administered intravaginally to one group of patients suffering from yeast infections of the vagina. A second group of such patients receive a suppository without the active ingredient of Example 4. A third group receives a suppository containing the drug clotrimazole, a commonly used drug for treatment of fungal infections of the vagina. Every 24 hours the process is repeated. within 2 days, the patients of the first group have no reddening of the vagina and within 7 days, a yeast culture produces negative results. The second group of patients continues to complain of itching and other common complaints of fungal infections. A yeast assay is positive. For patients in the third group, a yeast assay is negative; however, a number of these patients complain of irritation and in those patients, a significant reddening of the vagina is present.

EXAMPLE 13 - In vitro anti-microbial assay of the ozonide of linalool

A culture of E. coli was harvested with sterile saline using sterile swabs. The number of Colony Forming Units (CFUs) per ml in the suspension was determined by Standard Plate Count Method. A working suspension of E. coli with approximately $1.0 \times 10^7$ CFUs/0.1 ml was then prepared. Four aliquots of ml each of test ointment containing 1.0% ozonide of linalool were removed and placed in separate sterile screw-capped tubes. Each sample was inoculated with 0.1 ml of the working suspension of E. coli to yield a final concentration of approximately $1 \times 10^6$ CFUs/1 ml of the product. The samples were stored at 20°-25° C. for a total of 28 days. Samples were selected at 7 day intervals to determine the number of viable CFUs present. A control with uninoculated ointment was also stored with samples selected at the same intervals. At 7 days, and all subsequent sample selections, there were less than 10 CFUs present. No CFUs were present in any control sample.

EXAMPLE 14 Primary skin irritation test of ozonide of linalool

Six healthy New Zealand White rabbits were tested for skin irritation. Approximately four hours prior to application of the ozonide sample, the backs of the animals were clipped free of fur. Each rabbit received epidermal abrasions with a sterile needle at one test site while the skin at another test site remained intact. A 1.0% solution of linalool ozonide in isopropyl myristate was prepared. A 0.5 ml portion of the test solution was applied to each site by introduction under a double gauze layer to an area of skin approximately 1" square. The patches were covered with a nonreactive tape and the entire test site was wrapped with a binder. After 24 hours, the binders, tape, and test material were removed and the skin evaluated. The test material residue was removed with 70% isopropyl alcohol. An evaluation was also made at 72 hours after application. The reactions were scored according to the methods described in the Federal Hazardous Substances Act. The test solution had a Primary Irritation Index (PII) of 1.0. According to FHSA regulations, a material with a PII of less than 5.00 is generally not considered a primary irritant to the skin.

EXAMPLE 15 - Ocular irritation test in the rabbit of the ozonide of linalool

Six healthy New Zealand White rabbits were selected for study. The rabbits' eyes were judged free of irritation prior to the study by examining with a pen light and under UV light after installation of 2% fluorescein stain. A 1% solution of the ozonide of linalool was prepared in isopropyl myristate. A 0.1 ml portion of this test solution was instilled into the lower conjunctival sac of one eye of each rabbit. The lids were held closed for one second. The opposite eye of each rabbit received 0.1 ml of the isopropyl myristate, as control. Eyes were examined and the ocular reaction scored according to the "Illustrated Guide for Grading Eye Irritation by Hazardous Substances" (Appendix 1). At 24, 48, and 72 hours post dosing, the eyes were examined with a pen light and reexamined with UV light following fluorescein staining of the cornea. Under the conditions of this test, the test solution was considered a non-irritant to ocular tissues of the rabbit.

I claim:

1. A method of medical treatment for a medical condition in a mammal, said condition being selected from the group consisting of viral infections, bacterial infections, fungal infections, dermatoses, indolent neoplasms, sunburn, burns and swollen joints, said method comprising the parenteral application to said mammal of a pharmacologically effective amount for treatment of said condition of an ozonide of a termpene in a pharmacologically acceptable carrier or excipient.

2. The method of claim 1, wherein said terpene is selected from the group consisting of limonene, citronella, alphacarotene, beta-carotene, Vitamin A, linalool, linalyl acetate, squalene, geraniol, limonene, alphapinene, loganin, cymeme, farnesanes, eudesmanes, acoranes, cedranes, chamigranes, caryophyllanes, illudanes, humulenes, himachalenes, longifolanes, perhydroazulenes, quaianes, quaianolides, germacranes, labdane, clerodanes, abietic acid, phyllocladene, giberellins, ophiobolin A, retigeranic acid, gasgardic acid, lanosterol, euphol, oleanane, ursane, lupeol, hydroxyhopanone, lupanes, hopanes, B-selinene, zingibene, camphene, sabinene, ocimene, myrcene, nerol, citral A, citral B,. farnesol, bisabolene, phytol, and cecropia juvenile hormone.

3. The method of claim 1, wherein said parenteral application comprises systemic injection.

4. The method of claim 1, wherein said parenteral application comprises local injection.

5. The method of claim 1, wherein said terpene is a hemi-terpene, mono-terpene, sesqui-terpene, di-terpene, sis-terpene, tri-terpene, or tetra-terpene.

6. A pharmaceutical composition for the treatment of a medical condition in a mammal, comprising pharmaceutically effective amounts for treatment of said condition of an ozonide of a terpene in a pharmaceutically acceptable injectable carrier.

7. A pharmaceutical composition for the treatment of a medical condition in a mammal, comprising pharmaceutically effective amounts for treatment of said condition of an ozonide of a terpene in a pharmaceutically acceptable carrier for parenteral administration.

8. A method of treating fungal, bacterial, or viral infections in a mammal by administering an effective amount of a composition of claim 6.

9. A method of treating fungal infections of the skin or nails by administering an effective amount of a composition of claim 6 or 7.

10. A method of treating neoplasms by administering an effective amount of a composition of claim 6 or 7.

11. A method of treating acne by administering an effective amount of a composition of claim 6.

12. A method of preventing transmission of sexually transmitted diseases by administering a composition of claim 6.

13. A method of preventing pregnancy by administering an effective amount of a spermicidally effective composition of claim 6.

14. A method of treating swollen joints by injection of an effective amount of a composition of claim 6 or 7.

15. An ozonide of a terpene in combination with a non-aqueous pharmaceutically acceptable carrier.

16. A method of treating a medical condition in a mammal, said condition being selected from the group consisting of viral infections, bacterial infections, fungal infections, dermatoses, indolent neoplasms, sunburn, burns and swollen joints, said method comprising the injection application to said mammal of a pharmaceutical composition containing an ozonide of a terpene in a pharmaceutically acceptable injectable carrier, the amount applied of said composition being pharmaceutically effective in treating said condition.

* * * * *